US009204817B2

(12) United States Patent
Thiruvenkadam et al.

(10) Patent No.: US 9,204,817 B2
(45) Date of Patent: Dec. 8, 2015

(54) ATTENUATION CORRECTION IN POSITRON EMISSION TOMOGRAPHY USING MAGNETIC RESONANCE IMAGING

(75) Inventors: Sheshadri Thiruvenkadam, Bangalore (IN); Dattesh Dayanand Shanbhag, Bangalore (IN); Rakesh Mullick, Bangalore (IN); Florian Wiesinger, Freising (DE); Sandeep Suryanarayana Kaushik, Bangalore (IN)

(73) Assignee: General Electric Company, Niskayuna, NY (US)

( * ) Notice: Subject to any disclaimer, the term of this patent is extended or adjusted under 35 U.S.C. 154(b) by 701 days.

(21) Appl. No.: 13/451,250

(22) Filed: Apr. 19, 2012

(65) Prior Publication Data

US 2013/0281825 A1 Oct. 24, 2013

(51) Int. Cl.

| | |
|---|---|
| ***A61B 5/055*** | (2006.01) |
| ***G01R 33/48*** | (2006.01) |
| ***G01R 33/563*** | (2006.01) |
| ***A61B 6/03*** | (2006.01) |
| *G01R 33/485* | (2006.01) |
| *G01R 33/56* | (2006.01) |
| *A61B 6/00* | (2006.01) |

(52) U.S. Cl.

CPC ................. *A61B 5/055* (2013.01); *A61B 6/037* (2013.01); *A61B 6/5247* (2013.01); *G01R 33/481* (2013.01); *G01R 33/56383* (2013.01); *A61B 6/463* (2013.01); *A61B 6/582* (2013.01); *G01R 33/485* (2013.01); *G01R 33/5602* (2013.01)

(58) Field of Classification Search

CPC ........................................................ A61B 5/055
USPC .......................... 600/407, 410, 411, 425, 427
See application file for complete search history.

(56) References Cited

U.S. PATENT DOCUMENTS

| | | | | |
|---|---|---|---|---|
| 6,249,594 | B1 | 6/2001 | Hibbard | |
| 7,847,552 | B2 | 12/2010 | Haworth et al. | |
| 2003/0004408 | A1 * | 1/2003 | Zhu | 600/410 |
| 2007/0075248 | A1 | 4/2007 | Case et al. | |
| 2007/0167788 | A1 | 7/2007 | Hartlep et al. | |
| 2008/0135769 | A1 * | 6/2008 | Rosen | 250/363.09 |
| 2008/0253635 | A1 | 10/2008 | Spies et al. | |
| 2009/0074264 | A1 | 3/2009 | Pekar et al. | |
| 2009/0110256 | A1 | 4/2009 | Thielemans et al. | |
| 2010/0021034 | A1 * | 1/2010 | Lenglet et al. | 382/131 |
| 2010/0111390 | A1 | 5/2010 | Fenchel et al. | |

* cited by examiner

*Primary Examiner* — Peter Luong
(74) *Attorney, Agent, or Firm* — Robert M. McCarthy

(57) ABSTRACT

In one embodiment, a method includes performing a magnetic resonance (MR) imaging sequence to acquire MR image slices or volumes of a first station representative of a portion of a patient; applying a first phase field algorithm to the first station to determine a body contour of the patient in the first station; identifying a contour of a first anatomy of interest within the body contour of the first station using the first phase field algorithm or a second phase field algorithm; segmenting the first anatomy of interest based on the identified contour of the first anatomy of interest; correlating first attenuation information to the segmented first anatomy of interest; and modifying a positron emission tomography (PET) image based at least on the first correlated attenuation information.

18 Claims, 9 Drawing Sheets

ATTENUATION CORRECTION IN POSITRON EMISSION TOMOGRAPHY USING MAGNETIC RESONANCE IMAGING

BACKGROUND

In a positron emission tomography (PET) imaging system, a radionuclide is injected into a subject of interest. As the radionuclide decays, positrons are emitted that collide with electrons, resulting in an annihilation event that emits pairs of gamma particles. The pairs of gamma particles impact a detector array, which allows localization of the origin of the annihilation event. After a series of events are detected, localized concentrations of the radionuclide can be ascertained, leading to a functional diagnostic image.

As PET data is acquired, attenuation of some of the emitted photons may occur. Attenuation, or the phenomenon of reduction in the number of photons detected as compared to the amount of photons emitted, can lead to degraded image quality and reduced quantitative accuracy. Accordingly, in certain situations, such as patient imaging, PET imaging is combined with X-ray computed tomography (CT) imaging to correct for such attenuation. Because CT imaging is based on the attenuation of X-rays by the imaged target, the CT image can provide information relating directly to the attenuation coefficients of the materials (e.g., tissues) being imaged. To perform such correction, attenuation values are mapped to the CT image, and the effective energy used to generate the CT image is translated to PET energies.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a method includes performing a magnetic resonance (MR) imaging sequence to acquire MR image slices or volumes of a first station representative of a portion of a patient; applying a first phase field algorithm to the first station to determine a body contour of the patient in the first station; identifying a contour of a first anatomy of interest within the body contour of the first station using the first phase field algorithm or a second phase field algorithm; segmenting the first anatomy of interest based on the identified contour of the first anatomy of interest; correlating first attenuation information to the segmented first anatomy of interest; and modifying a positron emission tomography (PET) image based at least on the first correlated attenuation information.

In another embodiment, one or more tangible, non-transitory, machine-readable media storing instructions executable by a processor are provided. The instructions are configured to cause the processor to perform the acts of causing an MR imaging system to perform a magnetic resonance (MR) imaging sequence to acquire MR image slices or volumes of a first station representative of a portion of a patient; applying a first phase field algorithm to the first station to determine a body contour of the patient in the first station; identifying a contour of a first anatomy of interest within the body contour of the first station using the first phase field algorithm or a second phase field algorithm; segmenting the first anatomy of interest based on the identified contour of the first anatomy of interest; correlating first attenuation information to the segmented first anatomy of interest; and modifying a positron emission tomography (PET) image based at least on the first correlated attenuation information.

In a further embodiment, a hybrid positron emission tomography/magnetic resonance (PET/MR) imaging system is provided. The system includes an opening configured to receive a patient; a primary field magnet; a plurality of gradient field coils disposed about the opening; a radiofrequency (RF) transmit coil; a plurality of RF receiving coils; a photodetector disposed about the opening and configured to detect positron emissions from the patient to generate signals representative of the detected positrons; and control circuitry coupled to the gradient field coils, to the RF transmit coil, to the plurality of RF receiving coils, and to the photodetector. The control circuitry is configured to: apply control signals to the gradient, RF transmit and receiving coils to perform an MR imaging sequence to acquire MR image slices or volumes of a first station representative of a portion of the patient; process data generated by the photodetector as a result of detecting positrons to generate a PET image of the patient; and perform a PET image reconstruction process including: applying a first phase field algorithm to the first station to determine a body contour of the patient in the first station; identifying a contour of a first anatomy of interest within the body contour of the first station using the first phase field algorithm or a second phase field algorithm; segmenting the first anatomy of interest based on the identified contour of the first anatomy of interest; generating a continuous distribution attenuation map or a pseudo-CT image correlating first attenuation information to the segmented first anatomy of interest; and modifying the PET image based at least on the continuous distribution map or the pseudo-CT image.

BRIEF DESCRIPTION OF THE DRAWINGS

These and other features and aspects of embodiments of the present invention will become better understood when the following detailed description is read with reference to the accompanying drawings in which like characters represent like parts throughout the drawings, wherein.

DETAILED DESCRIPTION

Figure 1:
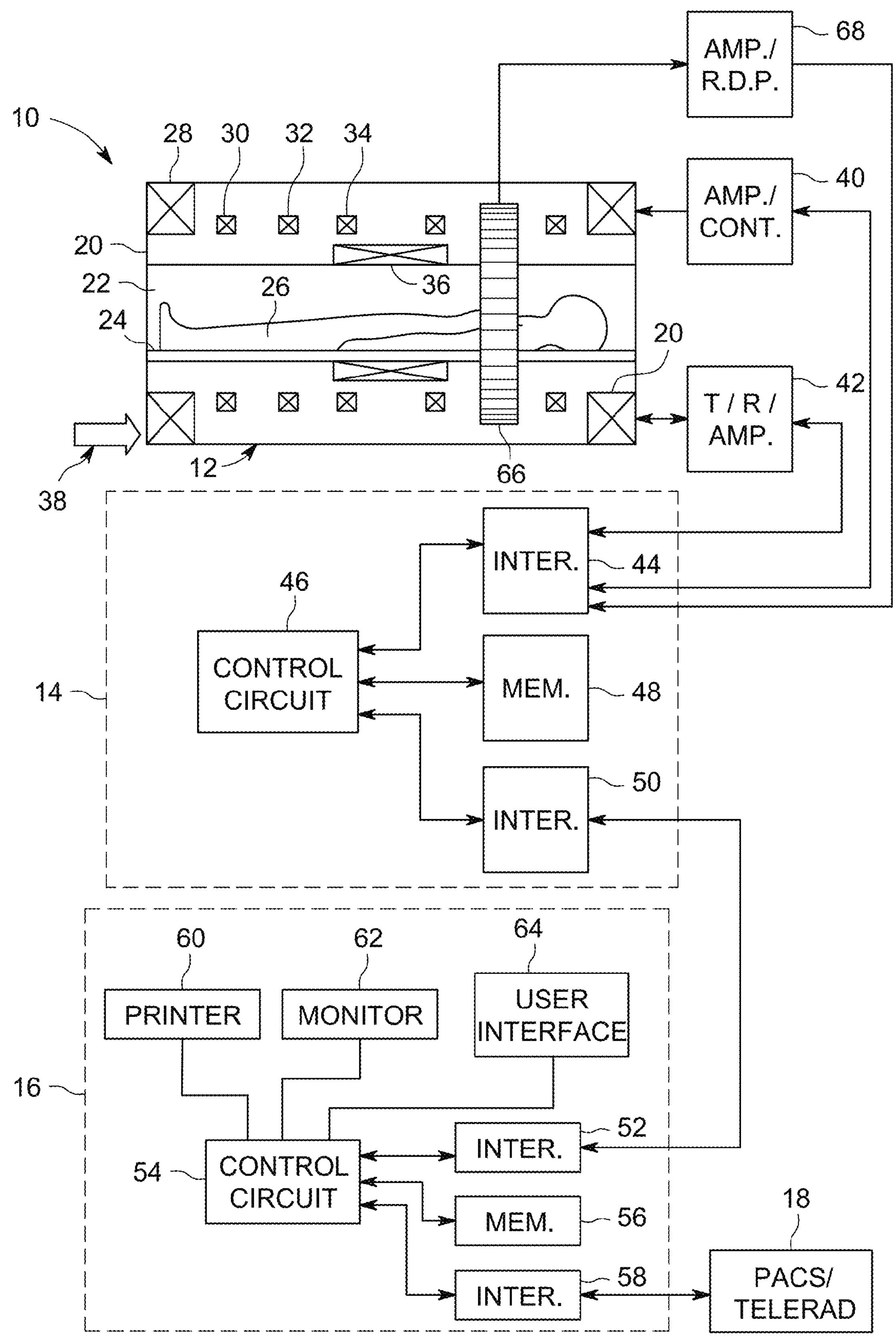
FIG. 1 is a system-level diagram depicting an embodiment of a hybrid positron emission tomography/magnetic resonance (PET/MR) imaging system configured to obtain attenuation-corrected PET and PET/MR images, in accordance with an aspect of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As noted above, the attenuation observed in PET images can be corrected using attenuation maps generated from CT images. However, it may be desirable to reduce the amount of radiation that the patient is subjected to during imaging. Accordingly, it may be advantageous if CT imaging could be replaced using non-radiation based imaging, such as magnetic resonance imaging (MRI).

In MRI, images are produced based on the characteristics of spinning gyromagnetic nuclei (e.g., hydrogen) within a subject of interest (e.g., hydrogen in water and/or fats). Generally, a highly uniform, static magnetic field is produced by a primary magnet to align the spins of the gyromagnetic nuclei. The nuclear spins are perturbed by an RF transmit pulse, encoded based on their position using gradient coils, and allowed to equilibrate. During equilibration, RF fields are emitted by the spinning, precessing nuclei and are detected by a series of RF coils. The signals resulting from the detection of the RF fields are then processed to reconstruct a useful image.

It should therefore be appreciated that the data provided by MR images relates to the varying nuclear spins of the gyromagnetic nuclei. Among other things, the spins of the nuclei are affected by their local environment, which enables MR data to provide information relating to the various tissues in which the nuclei are situated. Unfortunately, MR data does not directly relate to the attenuation of photons. However, it is now recognized that it may be possible to generate an attenuation map based on MR data by producing a tissue classification and or pseudo-CT image from which an attenuation map can be produced.

Indeed, the present embodiments include approaches for attenuation correction in PET images using MR data. For example, in accordance with present embodiments, MR data may be collected for a patient's entire body to produce image slices. Each image slice or volume (e.g., an image slab) or the entire 3D volume may be subjected to a phase field formulation, which detects the boundaries between tissues and background air, lungs and intra body air, air or metal, or similar boundaries. Indeed, the phase field algorithms described herein may enable enhanced boundary detection in 3D volumes, in which information from neighboring 2D slices or 3D volumes can be used. For example, in embodiments where gaps are detected in a boundary, it may be possible to fill the gaps using shared information between 3D data. Using the detected boundaries, a body mask may produced by stitching together the slices into stations and stitching the stations into the whole body image. Thus, the body mask may be a 3D representation of the patient's body contour. In addition to generating the body mask, the phase field formulation, using different sets of parameters, may also detect boundaries between tissues and lungs, air and lungs, water and lungs, and so on, to generate segmented anatomies of interest such as a lung mask delineating the 3D contour of the patient's lungs. Such methods may also be applicable to the patient's sinuses, bone structures, and other anatomies.

Using the body, lung, and sinus masks, the remaining tissues of the patient may be treated as fat, water, or a combination thereof, and the fat portion may be segmented to identify particular tissues. For example, cortical bone may be identified by detecting fat containership to distinguish bone marrow fat from organ fat. Such containership may be identified by sections of fat surrounded by dark regions in the MR image (corresponding to bone). Further, by detecting the cortical bone and its associated contour, the bone may be segmented to produce a cortical bone mask. Once the body, and internal structures such as lungs, fat, intra-body air, and other structures such as bone are segmented, known attenuation values can be tied to the structures in the body to generate an attenuation map for PET image reconstruction.

It should be noted that while the correction of PET and/or PET/MR images is discussed herein to facilitate the presentation of embodiments, the approaches described herein are also applicable to attenuation correction/image modification in other modalities, such as single photon emission computed tomography (SPECT). Therefore, while hybrid PET/MR imaging is presently discussed, it should be noted that the disclosed techniques are also applicable to hybrid SPECT/MR, SPECT image modification/attenuation correction, and any other imaging modality in which attenuation correction or attenuation-based modifications may be desirable.

The embodiments described herein may be performed sequentially, such as by first obtaining PET image data followed by the acquisition of MR image data and subsequent processing, or may be performed substantially simultaneously via the simultaneous acquisition of PET image data and MR image data. The acquisition of both types of image data may enable the generation of images having the spatial resolution and structural data associated with MR while also including the functional data produced by PET scans. Accordingly, in certain embodiments, a PET image produced from a given PET scan may be attenuation-corrected using MR data collected at substantially the same time as the PET scan. Because of the lower spatial resolution of PET compared to MR, it is now recognized that it may be desirable to perform anatomical identification and segmentation using fuzzy membership functions. Thus, in one embodiment, there may not be pixel-level accuracy for anatomical identification and segmentation. Indeed, as noted, certain of the present embodiments utilize phase field algorithms for structural identification.

A diagrammatic representation of an example hybrid PET/MR system 10, which may be configured to perform any one or a combination of the methods and techniques described herein, is shown in FIG. 1. In particular, the hybrid PET/MR system includes elements that are capable of acquiring and processing both PET and MR data, and also performing the PET image reconstruction approaches discussed herein. However, it should be noted that the present approaches are also applicable to sequential imaging, where either modality may be performed before the other to perform such reconstruction.

In particular, the hybrid PET/MR imaging system 10 is illustrated schematically as including a scanner 12, a scanner control circuit 14, and a system control circuitry 16. According to the embodiments described herein, the scanner control circuit 14 and the control circuitry 16 are generally configured to perform MR and PET imaging, such as imaging sequences capable of generating in-phase, out-of-phase, water, fat, and functional PET images. In one embodiment, the system 10 may be configured to generate at least the MR images within the same repetition time (TR). By way of non-limiting example, the system 10 may be configured to perform sequences such as Liver Acquisition with Volume Acquisition (LAVA) sequences, LAVA flex sequences, and reconstruction techniques such as Dixon and/or Iterative Decomposition of water and fat with Echo Asymmetry and Least squares estimation (IDEAL) techniques. The MRI contrast may be T1-weighted (T1w), proton density weighted (PDw), or T2 weighted (T2w), and may be optimized for segmenting a particular tissue type or to avoid certain artifacts. For example, in a T1 weighted image, the water within a bladder may skew the contrast in the region of the bladder. To overcome such contrast issues, the PD weighting may be increased.

System 10 additionally includes remote access and storage systems or devices as picture archiving and communication systems (PACS) 18, or other devices such as teleradiology equipment so that data acquired by the system 10 may be accessed on- or off-site. In this way, acquired data may be acquired, followed by on- or off-site processing and evaluation. Further, the PACS 18 enables communication with the imaging system 10, thus allowing a PET imaging sequence, MRI imaging sequence, and the attenuation correction process to all be performed in an automated fashion.

While the MRI system 10 may include any suitable scanner or detector, in the illustrated embodiment, the system 10 includes the full body scanner 12 having a housing 20 through which an opening or bore 22 is formed. A table 24 is moveable axially into the bore 22 to permit a patient 26 to be positioned therein for imaging selected anatomy within the patient. For example, in accordance with present embodiments, the patient 26 may be positioned on the table 24, and the system 10 may acquire MR data (e.g., MR image slices and/or volumes/slabs) in a station-wise manner. For example, a head station may be imaged first, followed by a chest or lung station, followed by an abdomen station, and so on.

Scanner 22 includes a series of associated coils for producing a controlled magnetic field and for detecting emissions from gyromagnetic material within the anatomy of the subject being imaged. A primary magnet coil 28 is provided for generating a primary magnetic field generally aligned with the bore 22. A series of gradient coils 30, 32, and 34 permit controlled magnetic gradient fields to be generated during examination sequences. A radio frequency (RF) coil 36 is provided for generating radio frequency pulses for exciting the gyromagnetic material, such as for spin perturbation or slice selection. A separate receiving coil or set of coils or the same RF coil 36 may receive magnetic resonance signals from the gyromagnetic material during examination sequences.

The various coils of scanner 22 are controlled by external circuitry to generate the desired field and pulses, and to read emissions from the gyromagnetic material in a controlled manner. In the illustrated embodiment, a main power supply 38 is provided for powering the primary field coil 28. Driver circuit 40 is provided for pulsing the gradient field coils 30, 32, and 34. Such a circuit may include amplification and control circuitry for supplying current to the coils as defined by digitized pulse sequences output by the scanner control circuit 14. Another control circuit 42 is provided for regulating operation of the RF coil 36. Circuit 42 may include a switching device for alternating between the active and passive modes of operation, wherein the RF coils transmits and receives signals, respectively. In certain embodiments, circuit 42 also includes amplification circuitry for generating the RF pulses and for processing received magnetic resonance signals.

Scanner control circuit 14 includes an interface circuit 44 which outputs signals for driving the gradient field coils and the RF coil and for receiving the data representative of the magnetic resonance signals produced in examination sequences. The interface circuit 44 is coupled to a control circuit 46. The control circuit 46 executes the commands for driving the circuit 42 and circuit 40 based on defined protocols selected via system control circuit 16. Control circuit 46 also serves to receive the magnetic resonance signals and performs subsequent processing before transmitting the data to system control circuit 16. Scanner control circuit 14 also includes one or more memory circuits 48, which store configuration parameters, pulse sequence descriptions, examination results, and so forth, during operation. Interface circuit 50 is coupled to the control circuit 46 for exchanging data between scanner control circuit 14 and system control circuit 16. Such data will typically include selection of specific examination sequences to be performed, configuration parameters of these sequences, and acquired data, which may be transmitted in raw or processed form from scanner control circuit 14 for subsequent processing, storage, transmission and display.

System control circuit 16 includes an interface circuit 52, which receives data from the scanner control circuit 14 and transmits data and commands back to the scanner control circuit 14. The interface circuit 52 is coupled to a control circuit 54 which may include a CPU in a multi-purpose or application specific computer or workstation. Control circuit 54 is coupled to a memory circuit 56 to store programming code for operation of the hybrid PET/MR system 10 and to store the processed image data for later reconstruction, display and transmission. For example, the programming code may execute one or more algorithms capable of performing PET image reconstruction based on acquired MR data, which will be discussed in detail below. An additional interface circuit 58 may be provided for exchanging image data, configuration parameters, and so forth with external system components such as remote access and storage devices 18. Finally, the system control circuit 54 may include various peripheral devices for facilitating operator interface and for producing hard copies of the reconstructed images. In the illustrated embodiment, these peripherals include a printer 60, a monitor 62, and user interface 64 including devices such as a keyboard or a mouse.

Scanner 12 and the control circuit 46 associated therewith produce magnetic fields and radio frequency pulses in a controlled manner to excite and encode specific gyromagnetic material within the patient 26. The scanner 12 and control circuit 46 also sense the signals emanating from such material and create an image of the material being scanned. In certain embodiments, the scan may be an accelerated or fully-sampled scan resulting in an array of data sets. The data sets, in accordance with present embodiments, may be representative of in-phase, out-of-phase, water, and fat images.

As noted above, the hybrid PET/MR system 10 is capable of multimodal imaging, and, in particular, is capable of collecting both MR and PET imaging data. Thus, the hybrid PET/MR system 10 additionally includes features enabling PET image formation. Indeed, data collection relating to positron detection may be performed substantially simultaneously with respect to the MR data collection.

In some PET imaging embodiments, a positron emitter may be administered to the patient 26, which produces positrons within the patient's body. The positrons interact with various electrons found within the patient's anatomy through an annihilation event, which produces gamma photons that may be detected and processed to create an image. In other embodiments, a radiotracer that emits the gamma photons is administered to the patient, and may be bound or taken up by particular tissues or organs. Typical radioisotopes include various radioactive forms of elements, although many in gamma ray imaging are based upon an isotope of technetium ($^{99}$Tc) that emits the gamma photons during decay. Various additional substances may be selectively combined with such radioisotopes to target specific areas or tissues of the body.

Accordingly, the hybrid PET/MR system 10 may include a photodetector 66 configured to detect photons emitted as a result of the annihilation or intrinsic emission events noted above. Again, the photodetector 66 may be used for various radionuclide imaging techniques including single photon emission computed tomography (SPECT) and positron emission tomography (PET). Although illustrated in the figure as a curved device positioned about the patient, in practice the detector 66 may be positioned below the patient, both above and below the patient, and may wrap partially around the patient. In general, the detector 66 may include one or more collimators and a plurality of scintillation crystals, together represented generally as reference numeral 66. The collimator allows gamma radiation emitted only in certain directions (typically perpendicular to the scintillator) to impact the scintillator. The scintillator, which may include a crystalline material, such as cerium-doped lutetium yttrium orthosilicate (LYSO), converts the received gamma radiation to lower energy light energy (e.g., in an ultraviolet range). In other imaging modalities, such as those that utilize X-rays, the scintillator may generate the lower light energy upon interaction with received X-rays. Detectors then receive this light and generate image data corresponding to photons impacting specific discrete picture element (pixel) regions.

The photodetector 66 is coupled, either directly or indirectly, to scanner control circuit 14 and system control circuit 16. In addition to the circuitry functions described above, this circuitry may include a number of physical and functional components that cooperate to allow the collection and processing of image data to create the desired images, and also for performing the PET image reconstruction methods disclosed herein. In certain embodiments, as illustrated, the system 10 may include raw data processing circuitry 68 that initially receives the data from the photodetector 66, and that may perform various filtering, value adjustments, and so forth. Scanner control circuitry 14, such as control circuit 46, or control circuitry 16, allows for the overall control of the imaging system, and for manipulation of image data. Circuitry 14 and/or circuitry 16 may also perform calibration functions, correction functions, and so forth on the data.

The circuitry 14, 16 may also perform image reconstruction functions, such as based on known algorithms (e.g., backprojection). In accordance with certain embodiments, as discussed herein, the circuitry 14 and/or circuitry 16 may perform PET image reconstruction using attenuation coefficients obtained using MR data. Indeed, as discussed herein such attenuation coefficients may be obtained directly from magnetic resonance imaging (MRI) data, a continuous distribution attenuation map, or from a pseudo-computed tomography (CT) image derived from pre-processed MR data. These and other approaches are discussed in further detail below.

Further, any post-acquisition functions of the circuitry 16 may, additionally or alternatively, be performed in post-processing on local or remote equipment (not shown). The circuitry 14, 16 may interact with interface circuitry 44 that enables control of the scanner and its components, including the patient support table 24, the photodetector 66, and so forth. In accordance with present embodiments, the memory circuitry 56 may store one or more sets of instructions that are executable by the circuitry 16 to generate attenuation-corrected PET images from attenuation data contained in MR mask images, pseudo-CT images, and/or attenuation coefficient values.

In the illustrated embodiment, the monitor 62 may display MR images, PET images, hybrid PET/MR images, reconstructed or attenuation-corrected PET images, or a combination thereof. Moreover, the images may be displayed in substantially real-time on the monitor 62. For example, the methods described herein may be performed prospectively such that as MR stations are acquired, the PET images displayed on the monitor 62 may be updated in substantially real-time. In other embodiments, the methods described herein may be performed retrospectively, such that the PET images displayed on the monitor 62 are only updated once all MR data has been collected and suitably processed.

In an institutional setting, the hybrid PET/MR imaging system 10 may be coupled to one of more networks to allow for the transfer of system data to and from the imaging system, as well as to permit transmission and storage of image data and processed images. For example, a local area networks, wide area networks, wireless networks, and so forth may allow for storage of image data on radiology department information systems or on hospital information systems. Such network connections further allow for transmission of image data to remote post-processing systems, physician offices, and so forth.

As noted above, aspects of the present disclosure include methods for performing attenuation correction on PET image data using acquired MR data. Thus, at least a portion of the disclosed methods may be performed by the system 10 described above with respect to FIG. 1. In some embodiments, the data processing techniques described herein may be performed at a separate workstation automatically or by a user, or automatically by system 10. It should be noted that subsequent to the acquisitions described herein, the system 10 may simply store the acquired data for later access locally and/or remotely, for example in a memory circuit (e.g., memory 56). Thus, when accessed locally and/or remotely, the acquired data may be manipulated by one or more processors contained within an application-specific or general purpose computer. The one or more processors may access the acquired data and execute routines including the image processing and reconstruction methods described herein.

Figure 2:
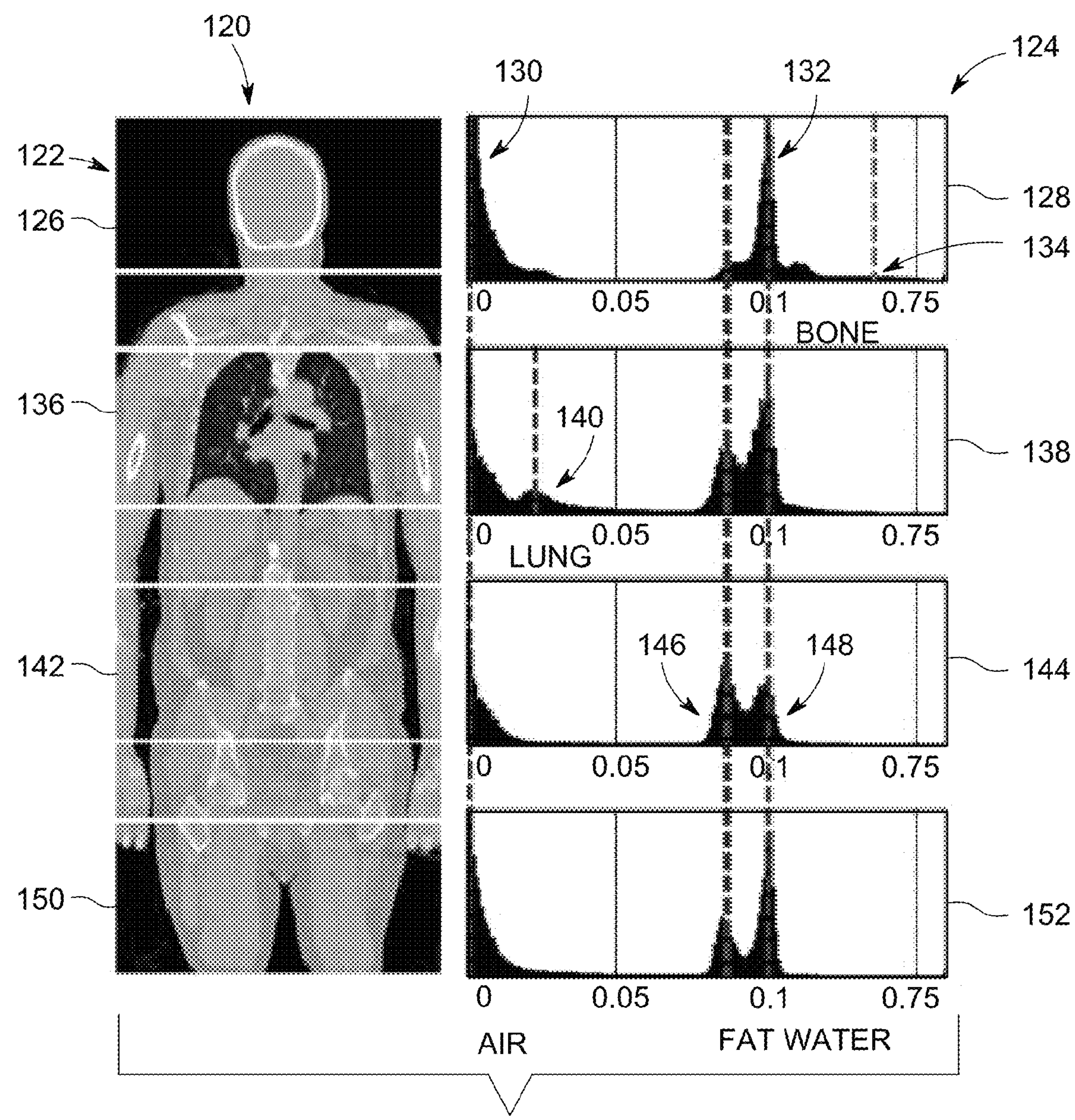
FIG. 2 is an example embodiment of a pseudo-computed tomography (CT) image having a plurality of stations with associated attenuation coefficient distributions, in accordance with an aspect of the present disclosure.

For example, referring to FIG. 2, imaging system 10 may produce an MR-based pseudo-CT image 120 of the patient 26, the image 120 having a plurality of stations 122 corresponding to various anatomical areas of the patient 26. The system 10 and/or processing device may also provide information relating to the attenuating features within each station 122. As illustrated, the attenuation information may be presented as a series of attenuation coefficient distributions 124 corresponding to each station. As illustrated, the distributions 124 include counts of particular attenuation coefficients within the stations 122, which is representative of the relative amount of each type of attenuating material within that particular station. For example, head station 126, which includes the patient's head and associated anatomies (e.g., brain, scull, sinuses), may have an associated attenuation coefficient distribution 128. As illustrated, attenuation coefficient distribution 128 includes several counts associated with air 130, with water 132, and a relatively high amount of counts attributable to bone 134 compared to the other stations 122. Similarly, a lung station 136 also includes a unique distribution 138. In particular, in the distribution 138, coefficients attributable to the lungs 140 appear at a higher attenuation coefficient than air. Additionally, an abdominal station 142 is depicted as having a distribution 144 in which there is a relatively large amount of fat-based and water-based attenuation 146, 148, and a leg station 150 is depicted as having a distribution 152 having a slightly higher water attenuation count than fat attenuation count.

Figure 3:
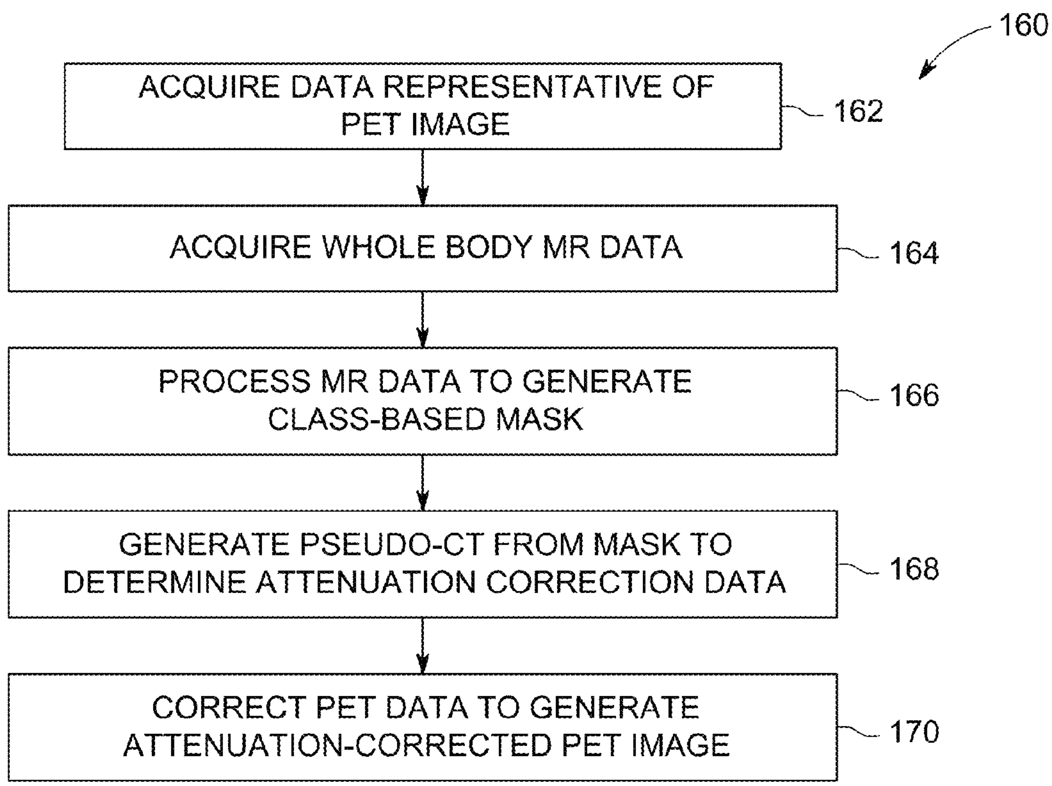
FIG. 3 is a process flow diagram depicting an embodiment of a method of PET image attenuation correction based on magnetic resonance imaging data, in accordance with an aspect of the present disclosure.

The pseudo-CT image 120 and station-wise attenuation data 124 described above may be generated during the course of an overall method 160 performed for PET attenuation correction by the systems 10, 50, and/or other processing device. Indeed, the image 120 and the data 124 may be output to another processing device, into the system 10, system 10, or any other device, for image reconstruction. An embodiment of the method 160 of PET attenuation correction is illustrated as a process flow diagram in FIG. 3.

As illustrated, the method 160 begins with acquiring (block 162) PET imaging data. For example, the patient 26 may be administered a radiopharmaceutical agent, placed within the imaging system 10, and imaged to generate the data. Before, during, or after acquiring the PET data, MR data may be acquired (block 164) from the patient 26. In accordance with present embodiments, the MR acquisition in block 164 may include a multi-parameter acquisition in which in-phase, out-of-phase, fat, and/or water images are obtained and either the magnitude or both the magnitude and phase images (e.g., real and imaginary components components of complex MRI data are stored). The different types of data may be obtained in the same TR, or in a different TR or with different MRI image contrast such as T1w, PDw or T2w. As noted above, such processes may include LAVA or LAVA flex acquisitions, and Dixon and/or IDEAL processing and generate additional maps such as T2*map.

Figure 5:
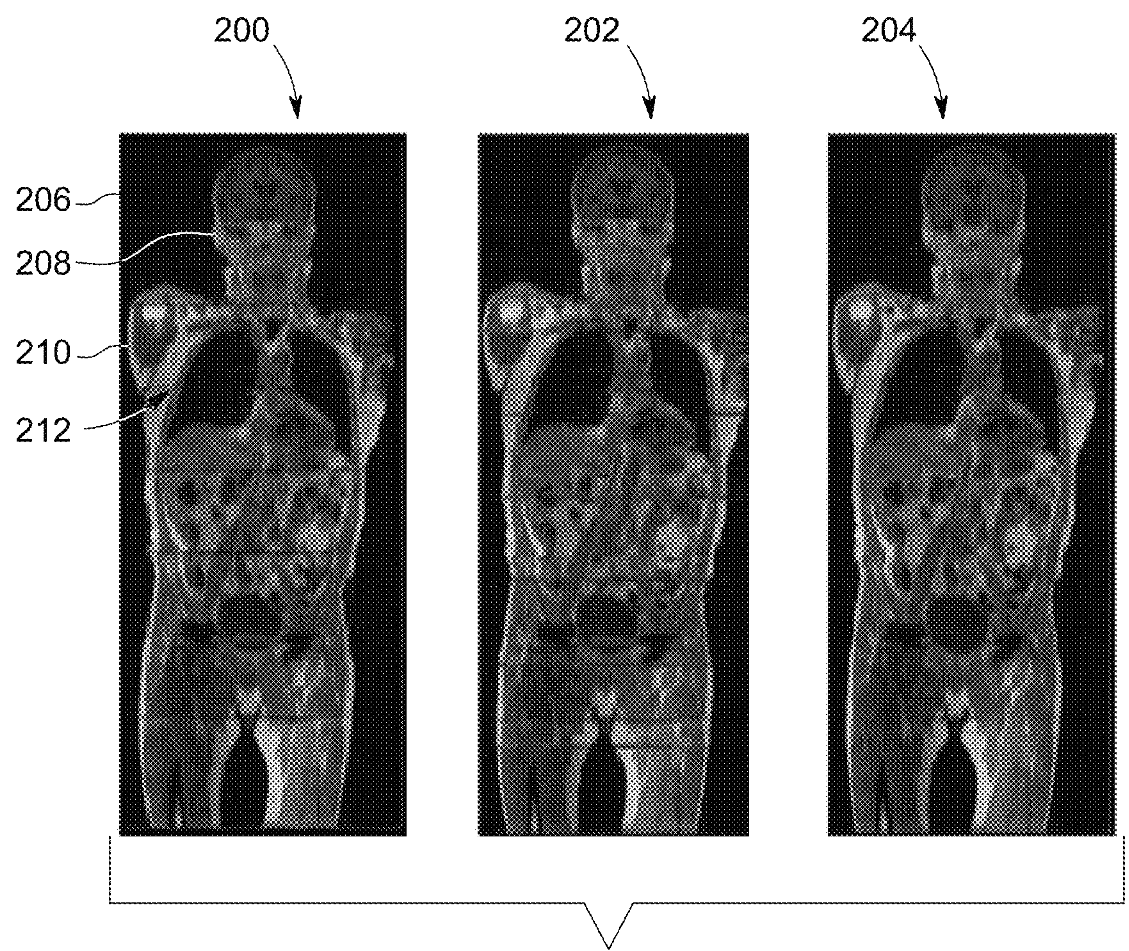
FIG. 5 is a combined illustration of embodiments of whole-body stitched images obtained using various stitching methods, in accordance with an aspect of the present disclosure.

The data obtained in accordance with block 164 may be processed to obtain one or more class-based masks. While discussed in further detail below with respect to FIG. 5, block 164 may include, among other steps, generating a body contour mask delineating the general outline of the patient's skin using a phase field formulation, generating masks for certain anatomies (e.g., the lungs), and segmenting certain portions of the patient image into classes such as fat, water, air, background, bone, and so on. The information so generated may be used to construct (block 166) a class-based mask having the segmented portions. These portions may be characterized as having certain attenuation correction factors or attenuation coefficients, and may be used to generate (block 168) a pseudo-CT image, such as the image 120 of FIG. 2.

The pseudo-CT image and its associated attenuation information, or, in other embodiments, attenuation data obtained from the classifications generated during MR image processing, may be used to correct (block 170) the originally-acquired PET image. For example, an attenuation map may be generated from pseudo-CT or MR data in which attenuation values may be correlated to particular tissues labeled during segmentation of certain of the MR images (e.g., fat and water images). The attenuation correction values tied to these masks may be correlated to particular areas of the PET image to correct those particular areas. By way of non-limiting example, the PET image may be corrected according to the following equation:

$$I_{AC} = I(l)\exp\left(\int_0^l \mu(x, y, E_0)\,dl'\right) \quad (1)$$

where $I_{AC}$ is the attenuation-corrected image, I(l) is the original, uncorrected image, and the term $$\exp\int_0^l \mu(x, y, E_0)\,dl'$$

represents an attenuation correction factor (ACF). The ACF, as may be appreciated, is a function of μ, the linear attenuation coefficient of the attenuating material (i.e., the product of the mass attenuation coefficient and the density of the attenuating material), $E_0$, the energy of the attenuated photons, and dl, the thickness of the attenuating material.

As noted above with respect to block 166, the present embodiments provide approaches toward PET attenuation correction using correction data obtained from MR images, and, in particular, via the generation of a body contour mask, various tissue masks, and a 4-class mask generating using phase field formulations as a method for contour detection of external and internal anatomies (e.g., the skin and the lungs). One embodiment of at least a portion of the acts according to block 166 is illustrated as a process flow diagram in FIG. 4.

Figure 4:
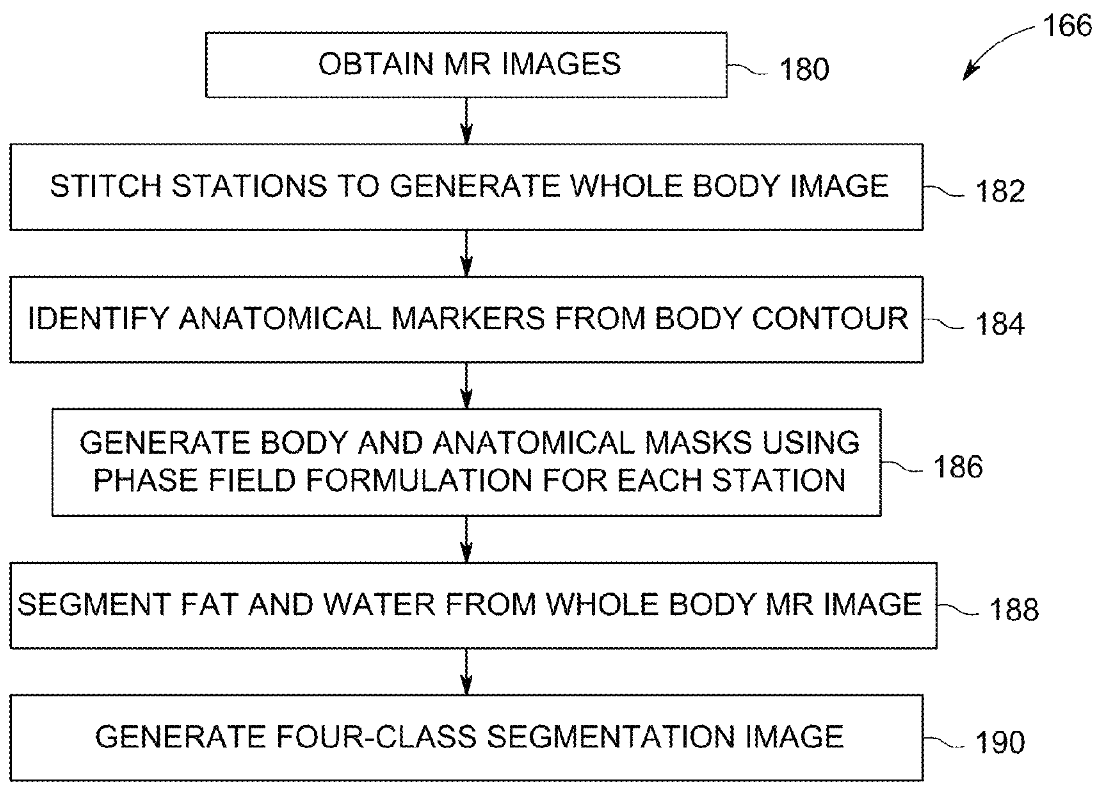
FIG. 4 is a process flow diagram depicting an embodiment of a method of generating a multi-class segmentation mask that may be used to generate a pseudo-CT image for PET image attenuation correction, in accordance with an aspect of the present disclosure.

In particular, FIG. 4 illustrates the method 166 by which MR data obtained from imaging methods (e.g., dual echo spoiled gradient echo such as LAVA-Flex) may be used to generate images useful for attenuation correction in PET images. Again, the method 166 may be performed by the system 10 or another processor-based device. Furthermore, any one or a combination of the stations described herein may be acquired according to the same or different MR data acquisition methods, such has LAVA, LAVA-flex, or similar acquisitions, or via other methods such certain short echo sequences, atlasing, and so on. Generally, one or more processor-based devices capable of performing instructions stored on a non-transitory, machine-readable medium such as a disc, nonvolatile memory, or the like may perform the method 166. The method 166 may be stored collectively on one or more non-transitory storage devices, and may be stored as one or more sets of instructions that are executable by one or more processors to perform the acts described herein.

The method 166 begins with obtaining (block 180) various MR images. The acts according to block 180 may include performing localization scans, registration scans, or the like, to register the patient's general position in the MR images to be obtained with the patient's position in the PET image(s). Once all preparatory images are obtained, the acts according to block 180 may include performing MR scans to obtain any one or a combination of in-phase ($I_i$), out-of-phase ($I_o$), water ($I_w$), and fat ($I_f$) images. In one embodiment, an acquisition performed within a single TR may obtain all four images for a particular slice selection. This type of acquisition may be performed for the whole body of the patient 26 such that block 180 amounts to a whole body MRI scan that produces $I_i$, $I_o$, $I_w$, and $I_f$ for each slice. In other embodiments, obtaining the images in accordance with block 180 may simply include accessing the data stored on one or more data storage devices.

It should be noted that upon obtaining the MR data in accordance with block 180, the steps described herein may not necessarily be performed according to the order presented. Therefore, while certain of the steps described herein are presented in a certain order, this order is not intended to limit the method to any particular order. However, the performance of some steps before others may enable increased accuracy in subsequent steps. For example, it may be desirable to perform anatomy localization before performing segmentation to enable enhanced segmentation.

After obtaining the MR images (block 180), the obtained image slices are combined (block 182) in a stitching process to generate stations. The stations may be representative of groups of anatomies delineated by particular recognizable body contour patterns, as discussed in further detail below with respect to FIGS. 9-12. Generally, the stations may be as illustrated in FIG. 2, but having MR data rather than pseudo-CT data. The stations may then be stitched together to form a whole body MR image. Various techniques for performing such stitching are discussed in further detail below with respect to FIG. 5. In addition, it should be noted that the method 166 may be performed prospectively or retrospectively. In prospective approach, the acts according to block 182 may not be performed immediately after acquiring each station. In other words, the acts according to certain of the blocks described below, such as blocks 184 and 186, may be performed before block 182 such that the PET image is modified on a station-wise iterative basis to generate updated PET or PET/MR images after each station-based update. In a retrospective approach, the acts may be performed as delineated in FIG. 4.

Thus, before, during, or after stitching images/stations in accordance with block 182, in accordance with present embodiments, various anatomical markers are identified (block 184) by detecting certain features in a body mask, by analysis of the body contour, based on digital imaging and communications in medicine (DICOM) information, based on user-provided input, or based on allometric ratios or based on information related to previously-acquired stations, or any combination thereof. The allometic ratios may be based on models or rules that certain anatomies occur in certain relative ratios. For example, the pelvis typically occurs two-thirds of the distance between the shoulders and crotch. In one embodiment, a head station may be differentiated from a lung station by detecting the characteristic contour of the shoulders. In other embodiments, mask information other than contour-related data may be utilized for anatomy detection. For example, once the head anatomy/station is detected, a lung station may be differentiated from an abdominal section based on the characteristic phase and signal differences in the lungs resulting from air. Examples of such identification are discussed below with respect to FIGS. 8-11. Generally, the acts represented by block 184 may delineate the whole body MRI images into different anatomical regions such as neuro, shoulders, thorax, abdomen, pelvis, and legs. As noted above, knowledge of a previously-acquired station may facilitate anatomical identification. For example, after acquiring a head station, the system 10 may recognize, or a user may input, that the station acquired immediately after the head station may be a lung station, and likewise the station after the lung station may be an abdominal station. Such prior knowledge may enable enhanced anatomy localization and segmentation by enabling the parameters of the phase field formulations described herein to be adjusted according to such knowledge.

Further, anatomical identification may also enable enhanced segmentation accuracy, especially between internal anatomies of the patient that have similar contrast and signal intensities. For example, during sinus segmentation, without any prior anatomical identification, an initial contour of the sinuses may erroneously include the temporal bones, as the sinus cavities and the temporal bone (which is pneumatized) have similar signal intensities and contrast. However, by prior anatomical identification, such as the head position, head size, and so on, the expected position of the temporal bones may be modeled and, based on particular complex MR signal variations, the sinuses may be segmented away from the temporal bones. Similarly, bones may be differentiated from intra-body air based on similar principles for other stations, such as the abdomen, pelvis, and leg stations.

The method 166 may also include generating (block 186) various masks using phase field formulations. For example, each image slice includes data representative of the location of the patient's skin boundaries (e.g., MR data representative of subcutaneous fat), which is detected using phase field approaches. The skin boundaries delineate the body contour of the patient 26. The identification of the body contour may enable a more accurate initial estimate for lung, body air, and fat/water segmentation discussed below. Further, organ localization enables the optimization of segmentation parameters for the lungs and body air.

In addition, certain image slices may include contours representative of internal anatomies. For example, some slices through the patient's chest may include internal data representative of the contour of the lungs and/or trachea. Such data can be useful for generating accurate attenuation maps, as the lungs may attenuate certain photons to a different degree than air and other tissue containing large amounts of fat and water. Such approaches are discussed in further detail below with respect to FIGS. 6 and 7.

The phase field formulation approaches described herein may also enable bone segmentation. For example, the phase field formulations discussed herein may be utilized to determine an outer contour of fat that is bounded by dark structures within MR images. This is referred to herein as the "containership" of the fat in marrow by cortical bone. Therefore, by modeling a containership of marrow fat, the present embodiments provide for the generation of a cortical bone mask for segmentation.

The method 166 also includes segmenting (block 188) fat and water volumes from the whole body MR images. In accordance with present embodiments, the fat volumes may be segmented using the $I_f$, $I_w$, and $I_i$ channels obtained in block 180 using a two-step process. The two-step process includes a first step of estimating the intra-body air statistics to set a threshold for the intra-body air. This removes the air component from the fat and water channels of the images to obtain a coarse estimate of fat and water components, which may be represented by $I_{fl}$ and $I_{wl}$, respectively.

In a second step, fat $I_{ffr}$ and water $I_{wfr}$ fraction images are obtained. For example, the fat and water fraction images may be obtained based on the relationship that the in-phase image is the sum of the water and fat images ($I_i=I_f+I_w$). The fat and water fraction images may be represented by $I_{ffr}=I_f/I_i$ and $I_{wfr}=I_w/I_i$.

Figure 12:
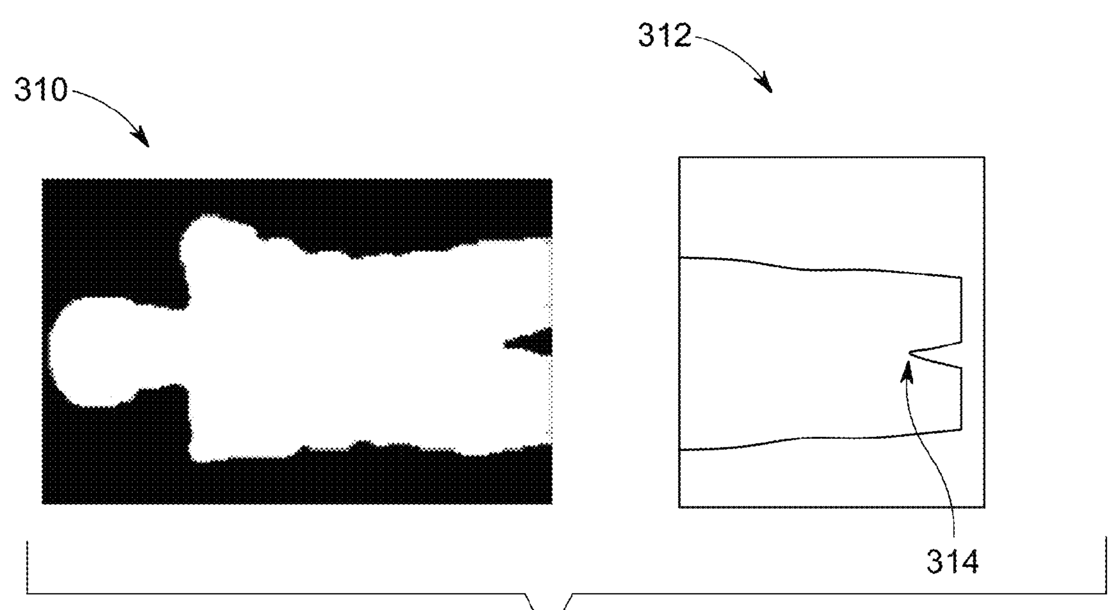
FIG. 12 is an embodiment of a body mask illustrated along a coronal plane of the patient, and a plot denoting the contour of the body mask as a function of position along the coronal plane, in accordance with an aspect of the present disclosure.

The fat components and water components are also obtained based on these relationships. In particular, the fat component is obtained as $I_f=(I_{ffr}\geq 0.5)\cap I_{fl}$ and the water component is obtained as $I_w=(I_{wfr}\geq 0.5)\cap I_{wl}$. In other words, the fat component is defined as the overlap between the values in the fat fraction image having a value greater than 0.5 and the values in the coarse estimate of the fat component. Similarly, the water component is defined as the overlap between the values in the water fraction image having a value greater than 0.5 and the values in the coarse estimate of the water component. Example images resulting from the steps performed in block 188 are illustrated in FIG. 12.

Figure 13:
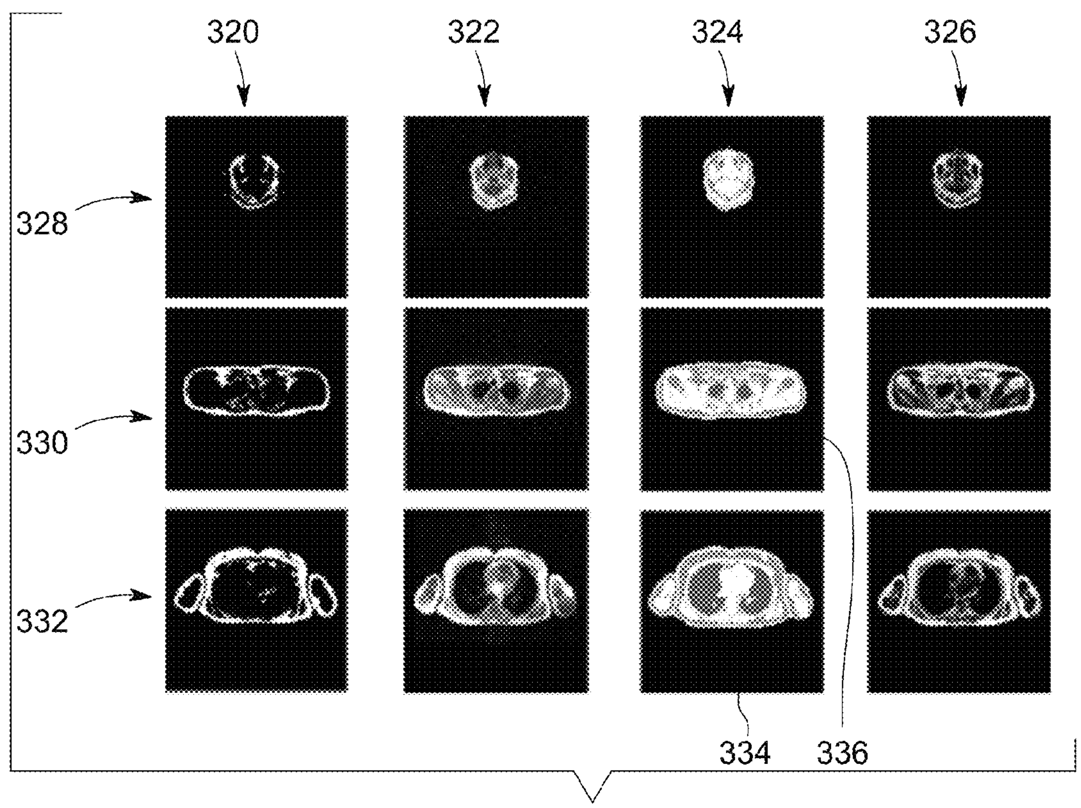
FIG. 13 is an embodiment of a plurality of images including a series of CT fat images, a series of MR in-phase images, a series of fat-water segmented MR images, and a series of MR fat fraction images, in accordance with an aspect of the present disclosure.

Once the fat and water components have been segmented from the whole body MR image, a four-class segmentation image is generated (block 190) in which fat, water, lungs, and the combination of background, metal, and bone are each represented as having a particular attenuation value. The four-class segmentation image provides tissue classification for the generation of a pseudo-CT image for attenuation correction in PET images, or for direct attenuation correction in PET images. An example four-class segmentation image is illustrated in FIG. 13 and discussed in further detail below.

As noted above, to enable accurate segmentation and to obtain a single contiguous scan image, the MR images/stations obtained in accordance with block 180 are stitched in block 182. An example of stitched MR data is provided in FIG. 5, which illustrates whole-body MR images that have been stitched according to different stitching protocols. In particular, a first image 200 resulting from an automatic binding stitching method, a second image 202 resulting from a signal-to-noise ratio (SNR) stitching method, and a third image 204 resulting from a non-extreme slices stitching method, are illustrated.

Keeping in mind that each station of each of the images 200, 202, 204 include several slices, each of the methods mentioned above (i.e., automatic binding, SNR, non-extreme slices) utilize an overlap between adjacent stations. For example, as illustrated, image 200 includes a neuro station 206, a lower head station 208, and an upper lung station 210 each disposed adjacent to the next. Divisions 212 are also visible between each station. In each of the stitching methods mentioned above, an overlap in slices between adjacent stations is utilized. For example, to stitch the lower head station 208 to the upper lung station 210, in each method, an overlap between 5, 10, 15, 20, or more image slices may be utilized to determine overlap and also to determine which image slices (i.e., which image slices selected from the overlapping stations) will be displayed at areas proximate the divisions 212. A schema 220 depicting such an arrangement is illustrated in FIG. 6.

Figure 6:
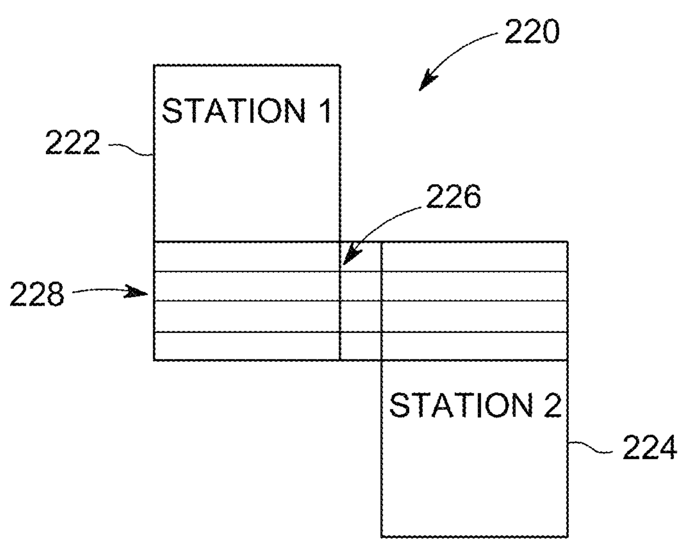
FIG. 6 is a diagram depicting an embodiment of the manner by which image slices of different stations may overlap, in accordance with an aspect of the present disclosure.

In FIG. 6, the schema 220 includes a first station 222 and a second station 224. The first and second stations 222, 224 overlap in a region 226 that includes a plurality of image slices 228 from each station. Each of the methods used to produce the images 200, 202, 204 in FIG. 6 utilizes the plurality of slices 228 differently to determine what is displayed within the region 226 in the stitched image.

In each of the methods, a particular number of slices for the plurality of slices 228 may be chosen (e.g., 5, 10, 15, or more). The first and second stations 222, 224 may then be stitched together by an overlap of the slices that are closer to the other station. For example, the slices in the first station 222 closest to the second station 224 may be chosen, and vice versa. In the automatic binding method used to produce image 200, the stitching may simply include displaying, in the region 226, the image slices corresponding to the second station 224.

In the SNR method used to produce image 202, the slices in the plurality of slices 228 having the higher SNR may be chosen. In other words, in the SNR method, the slices that are displayed within the region 226 may belong to the first station 222, or the second station 224, or a combination thereof. To determine which slice has the higher SNR, a calculation of the SNR for each slice is performed according to the equation:

$$SNR = \frac{\sigma S}{\sigma N} \qquad (2)$$

where σS is the standard deviation of the signal patch and σN is the standard deviation of the background (noise) patch.

In the non-extreme slices method used to produce the image 204, the slices of the first station 222 are chosen for a first portion of the region 226 (e.g., the first 10 slices). Slices from the second station 224 are chosen for the lower portion of the region 226 (e.g., the last 5 or 10 slices).

To enable enhanced stitching and to enable continuity across different scans, which may be performed by different technicians, the stations may be tied to particular field ID's and field descriptions within a digital imaging and communications in medicine (DICOM) protocol. Indeed, such field entries and identification may enable communication and standardization across different platforms (e.g., scanners, servers, workstations), and enables integration in the PACS system discussed with respect to FIG. 1. Indeed, continuity may be obtained using the information from the fields in the DICOM header set forth below in Table 1.

TABLE 1

| DICOM field ID | DICOM field description |
|---|---|
| 0008, 103E | Series Description |
| 0020, 000E | Series Instance UID |
| 0020, 0011 | Series Number |
| 0020, 0013 | Image (Instance) Number |

Similarly, overlap between stations may be detected by matching the following DICOM header field in Table 2.

TABLE 2

| DICOM field ID | DICOM field description |
|---|---|
| 0020, 0032 | Image (Patient) Position |

Figure 7:
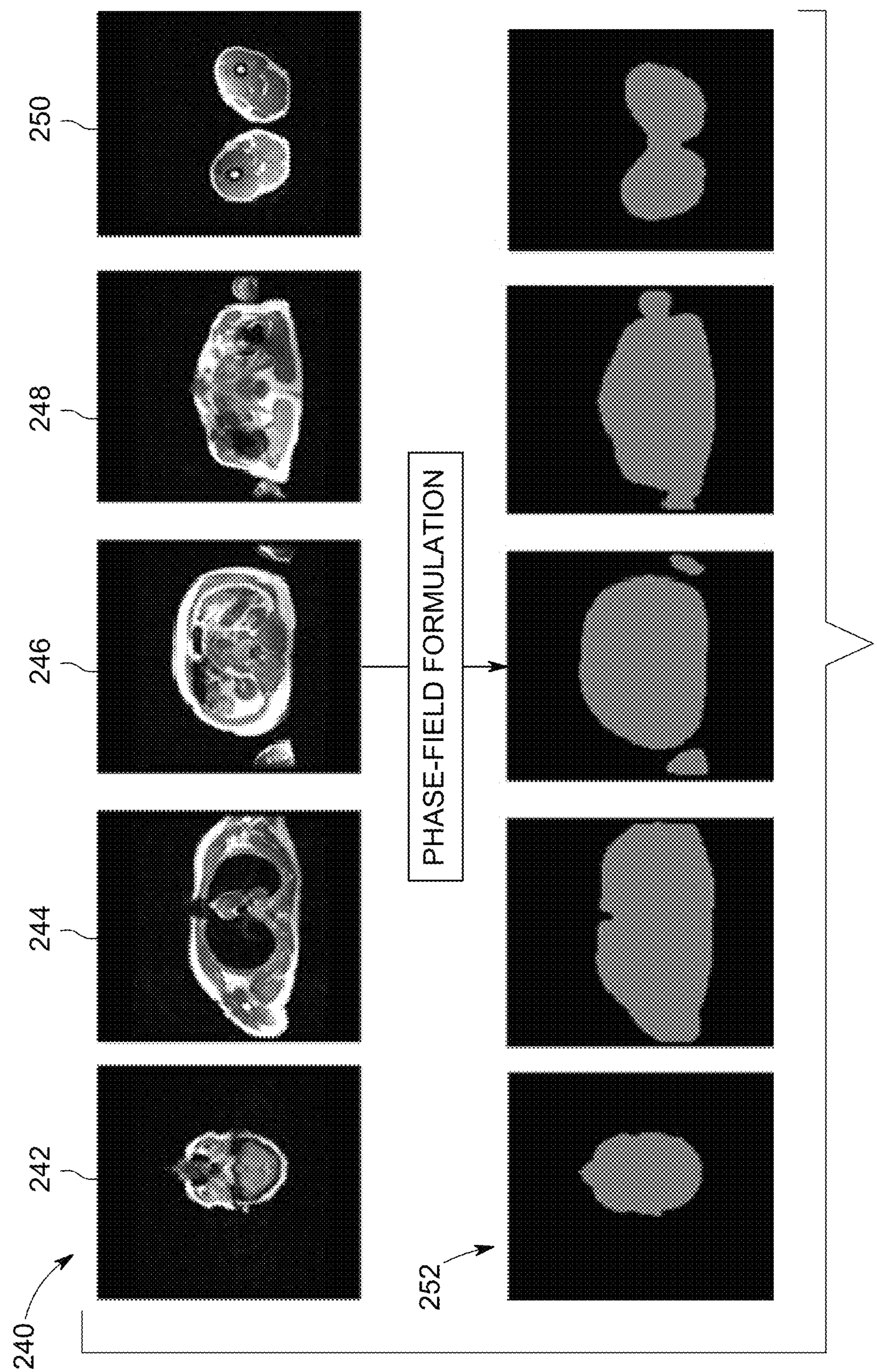
FIG. 7 is an embodiment of a series of 2D MR image slices and their associated body masks generated using a phase field formulation to detect tissue-air boundaries, in accordance with an aspect of the present disclosure.

To facilitate anatomy detection within each station, as noted above with respect to FIG. 4, a body mask is generated (i.e., the body is segmented) using a phase field formulation. In accordance with present embodiments, the phase field formulation may be performed on an image-by-image basis or on the entire 3D volume using 3D neighbor information to detect skin boundaries (i.e., the body contour), and, in certain of these embodiments, to delineate certain internal anatomies such as the sinuses, lungs, and trachea. Indeed, the phase field algorithms described herein may enable enhanced boundary detection in 3D volumes, in which information from neighboring 2D slices or 3D volumes can be used. For example, in embodiments where gaps are detected in a boundary, it may be possible to fill the gaps using shared information between 3D data. FIG. 7 depicts an example of image slices analyzed using a phase field formulation in accordance with present embodiments.

In particular, FIG. 7 depicts a plurality of 2D MR images 240 of various anatomies of the patient 26, including a head slice 242, a lung slice 244, an abdominal slice 246, a pelvic slice 248, and a leg slice 250. In accordance with present embodiments, each slice is subjected to the phase field formulation discussed herein to identify regions corresponding to the fat signal from sub-dermal fat (i.e., for skin segmentation). In particular, the regions corresponding to the skin define boundaries for segmentation of the body mask, as illustrated by a plurality of mask slices 252 corresponding to each of the image slices 240.

To generate the body mask slices 252, a volume treatment is performed using the phase field formulation, which in certain embodiments, may be a 2-class phase field formulation represented by the following equation:

$$E[u] = \int_\Omega (1-u)^2 (I - c_{air})^2 dx + \int_\Omega u^2 \frac{\alpha}{1+\beta(I-c_{air})^2} dx + \tilde{\lambda} \int_\Omega u^2 (1-u)^2 dx + \lambda \int_\Omega |\nabla u|^2 dx \tag{3}$$

or $$E[u] = \int_\Omega (1-u)^2 \|I - c_{air}\|^2 dx + \int_\Omega u^2 \frac{\alpha}{1+\beta\|I-c_{air}\|^2} dx + \tilde{\lambda} \int_\Omega u^2 (1-u)^2 dx + \lambda \int_\Omega |\nabla u|^2 dx$$

where I is a weighted metric of signal intensity and image gradients from $I_i$, $I_w$, and $I_f$ data. Indeed, unlike thresholding or similar methods, the present embodiments use complex MR image data including both magnitude and phase information as inputs into the multi-parametric phase-field based segmentation methods described herein, and, in particular, into equations 3 and 4 discussed herein. The energy of the equation is minimized over the binary indicator functions of $u(x) \in \{0,1\}$. The term u represents the two-class function (i.e., u is either 0 or 1), with u=0 representing background and u=1 representing tissue. Parameters α, β, and λ represent noise variance, smoothness, and sensitivity, and may be manually set. In particular, β relates to the standard deviation of the background distribution, and λ captures the scale of the segmentation used to produce an accurate contour. It should be noted that, for finer, internal anatomies of interest, varying values for λ may be used. For example, a smaller value for λ may be used for a station encompassing the trachea as compared to a value of λ that may be used for a station encompassing the bulk of the lungs. Further, these parameters may be validated empirically and/or may be cross-validated using clean slices. The equation of (3) is minimized using descent. The descent equation is solved using a semi-implicit iterative method in a multi-resolution framework. Thresholding of u may also be performed every few iterations to maintain the value of u in {0, 1}. By way of non-limiting example, the initial mask produced using this method may be set to between 1 and 10 pixel widths from the calculated boundary, and $c_{air}$ may be set using an initial region. Values for $c_{air}$ may also be added to updates.

Regarding the components of equation (3), the term $$\int_\Omega (1-u)^2 (I - c_{air})^2 dx$$

seeks an intensity close to $c_{air}$ in region u=0, $$\int_\Omega u^2 \frac{\alpha}{1+\beta(I-c_{air})^2} dx$$

seeks an intensity different from $c_{air}$ in region u=1, $$\tilde{\lambda} \int_\Omega u^2 (1-u)^2 dx$$

constrains u to be {0, 1}, and $$\lambda \int_\Omega |\nabla u|^2 dx$$

is a smoothing term for u. These various parameters enable the formation of masks with higher fidelity than would be obtained using other techniques such as thresholding. For example, the terms above may reduce or prevent the formation of gaps in body masks that can result from techniques such as thresholding.

Further, the use of equation (3) enables the variation of parameters on a station-wise or anatomy-wise basis or contrast-to-noise/signal to-noise variations to obtain enhanced segmentation. For example, meta-data may be tied to particular regions of the patient's anatomy, which enables each of the parameters α, β, and λ to be set to a value correlative to the meta-data. For example, any one or a combination of these parameters may be suitably adjusted based on meta-data related to regions of the body.

As noted above, in addition to generating a mask of the patient's body contour, the present approaches also provide techniques for generating particular tissue masks for segmentation (i.e., for one or more anatomies of interest). For example, in accordance with certain embodiments, the acts represented by block 186 may generate lung and/or sinus masks and/or within body air masks in addition to the body mask. Indeed, the present techniques also enable the separate segmentation of lungs and air using multiple channels generated from the acquisition in block 180. It should be noted that the approaches described herein are capable of addressing artifacts in MR images resulting from the presence of a metal, such as a suture. For example, within each image, the artifacts attributable to metal may be isolated. Gradients may then be used to smooth the regions in the image proximate the area of the metal, and the artifacts may be removed at a later stage by connected component analysis. Further, the parameters of equation (3) may be suitably adjusted using prior meta-information regarding the presence of the metal in a particular station.

Figure 8:
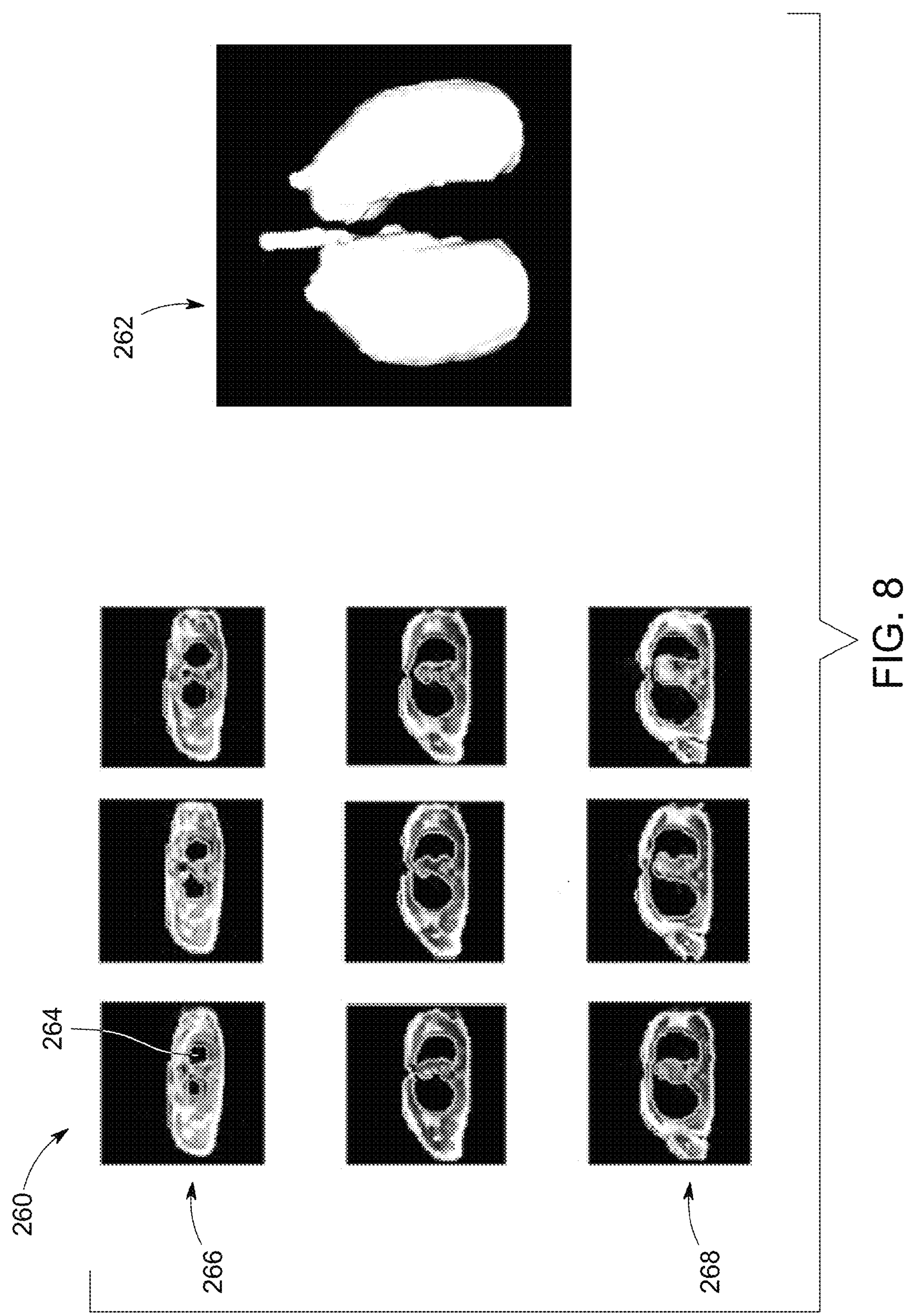
FIG. 8 is an embodiment of a series of 2D MR image slices through a lung station each having a boundary between tissue and lung as determined using a phase field formulation, and the lung mask resulting from the combination of their detected boundaries, in accordance with an aspect of the present disclosure.

Referring now to FIG. 8, a series of MR slices 260 through the lungs are illustrated, along with a 3D lung mask 262 resulting from the segmentation process. In particular, each of the MR slices 260 is subjected to a phase field formulation in accordance with equation (4) below.

$$E[u] = \int_{\Omega_{body}} (u)^2 \|I - c_{lungs}\|^2 dx + \int_{\Omega_{body}} (1-u)^2 \frac{\alpha}{1 + \beta\|I - c_{lungs}\|^2} dx + \tilde{\lambda}\int_{\Omega_{body}} u^2(1-u)^2 dx + \lambda\int_{\Omega_{body}} |\nabla u|^2 dx. \quad (4)$$

It should be noted that while equations (3) and (4) are similar, the parametric values for α, β, and λ are different than the values for body segmentation. In particular, for body segmentation, to avoid incorrectly classifying interior air pockets as background, the above parameters and the gradient descent time step are chosen carefully to prevent segmentation of interior contours. Additionally for lung segmentation, the indicator function, u, is reversed compared to equation (3). In other words, u=0 corresponds to tissue and u=1 corresponds to the lungs. The initial contour for lung segmentation is the body mask.

The phase field formulation, applied for lung segmentation, enables the detection of the lung contour within the body cavity, as illustrated within each of the slices 260. In particular, each of the slices 260 includes a marker 264 delineating the detected contour of the lungs. Thus, in a first set 266 of the slices 260, which are images of the lungs taken in a transverse plane of the patient 26 proximate the trachea (i.e., the posterior end), the contour of the lungs appear relatively small. A second set 268 of the slices 260 illustrate the detected contour of the lungs toward their anterior end proximate the diaphragm. Thus, the markers 264 in the second set 268 illustrate a larger contour of the lungs. The detected contour of the lungs in each of the slices 260 may be combined (e.g., in the stitching process) to generate the 3D lung mask 262, which is used during the generation of the 4-class body mask noted above and discussed in further detail below.

As noted above with respect to FIG. 4, certain of the stations within the whole body MR image (i.e., the stitched MR image) may be automatically identified to facilitate the segmentation of particular structures. The present embodiments provide for the detection of a number of stations based on a variety of anatomical markers. For example, the shoulders, the lungs, the pelvis, and the crotch may all be used to identify stations, as discussed below with respect to FIGS. 9-12. Such station identification enables information to be derived for each station such as organ context, organ localization, signal-to-noise and contrast-to-noise based metrics for the tuning of the segmentation parameters α, β, and λ of equations (3) and (4).

Figure 9:
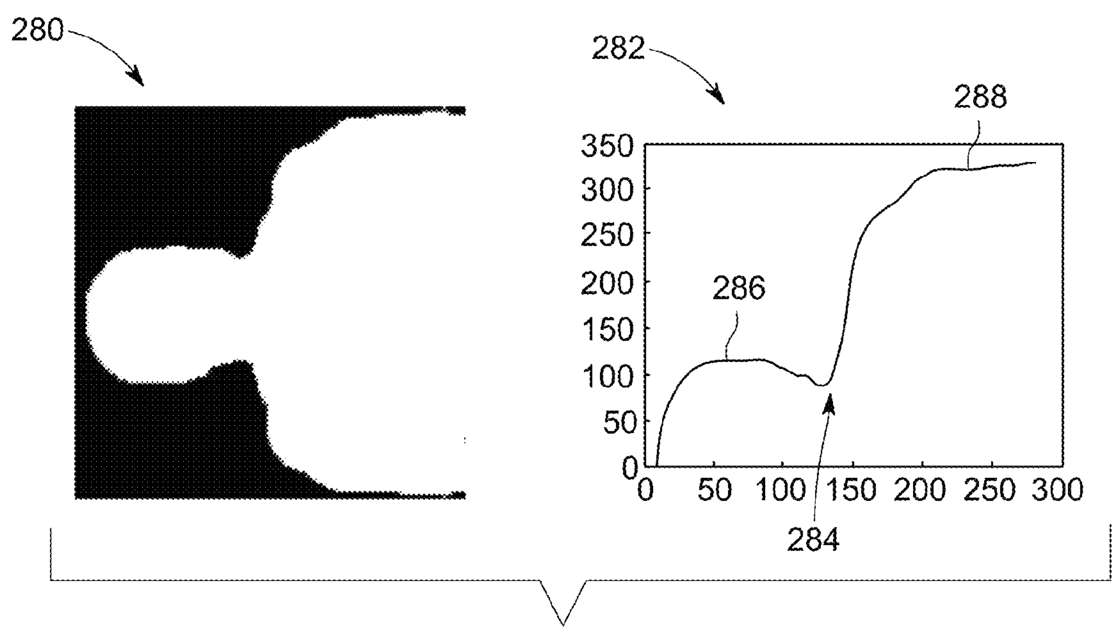
FIG. 9 is an embodiment of a body mask and a plot denoting the contour of the body mask as a function of position along the patient's sagittal line, in accordance with an aspect of the present disclosure.

FIG. 9 illustrates a portion 280 of the body mask through the patient' coronal plane that is generated in accordance with block 186 of FIG. 4, as well as a plot 282 of the mask contour as a function of position along the patient's sagittal line. As depicted in the plot 282, a local minimum 284 in the mask contour is observed at the position corresponding to the shoulders. Accordingly, the shoulder line may be demarcated using the local minimum 284 in reference to a signal representative of the head 286 and a signal representative of the chest region 288.

Figure 10:
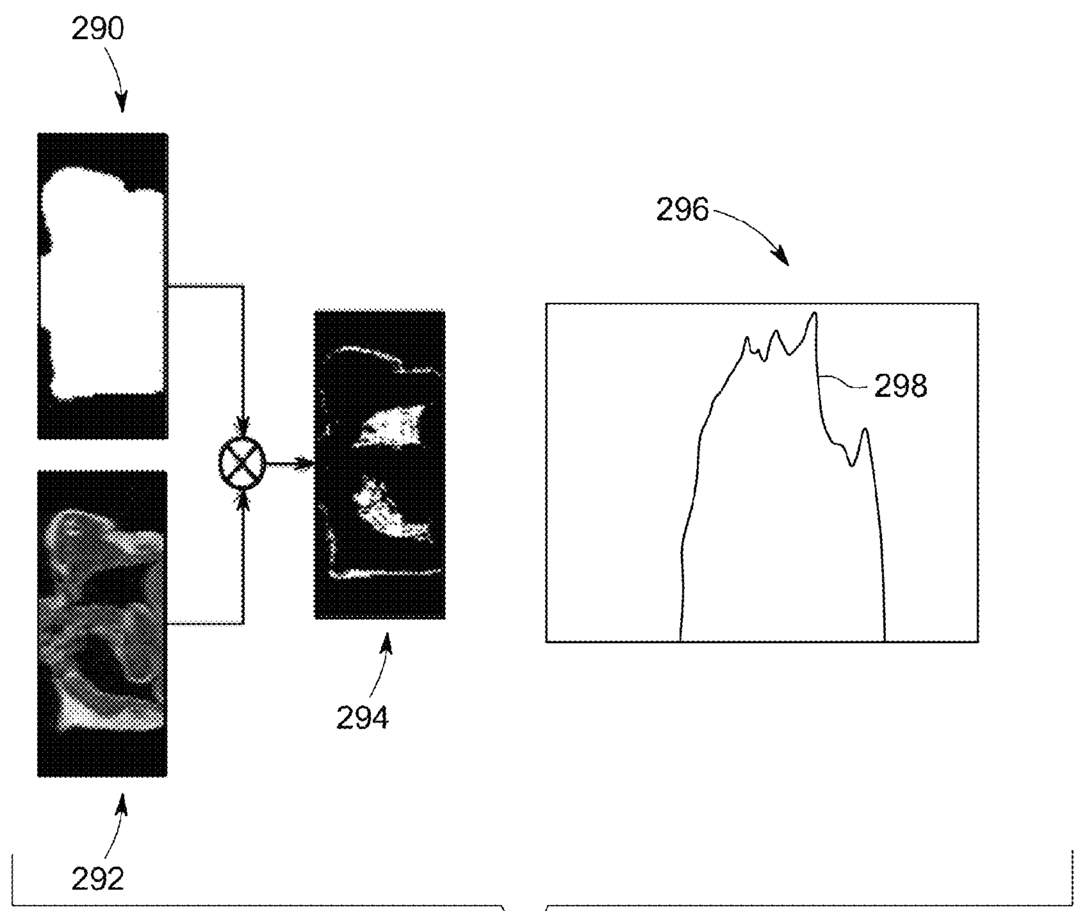
FIG. 10 is an embodiment of a combination of a body mask and an MR image combined to detect a lung station, and a plot denoting the air signal intensity associated with their combination as a function of position along the patient's sagittal line, in accordance with an aspect of the present disclosure.

The lungs may be automatically detected based on signal thresholding, as illustrated in FIG. 10. FIG. 10 depicts a portion 290 of the body mask in a coronal plane, along with a lung station having MR data 292. In accordance with present embodiments, the position of the lungs may be detected by detecting signal thresholds resulting from the presence of air in the chest. For example, the portion 290 of the body mask and the lung station 292 are combined to generate a data-mask image 294. As illustrated in the image 294, the mask portion 290 is used as a background against the MR data in the station 292.

Thus, the areas in the image 294 having a large mask intensity correspond to regions that are not blocked by the MR data, i.e., regions having little to no MR signal. Such regions, in the chest, correspond to the presence of the lungs. Accordingly, in a plot 296 of the mask intensity as a function of position along the sagittal line, a large intensity peak 298 may correspond to the position of the lungs. Further, it should be noted that the position of the lungs may be detectable in this manner via a threshold observed using transverse slices taken from the anterior to posterior ends, as well as coronal slices taken from the ventral side of the patient to the dorsal side of the patient. Indeed, the air threshold may be detected in three dimensions using the relationship illustrated in FIG. 10 and also using the upper half of the coronal plane and mid-coronal slices on the sagittal line.

Figure 11:
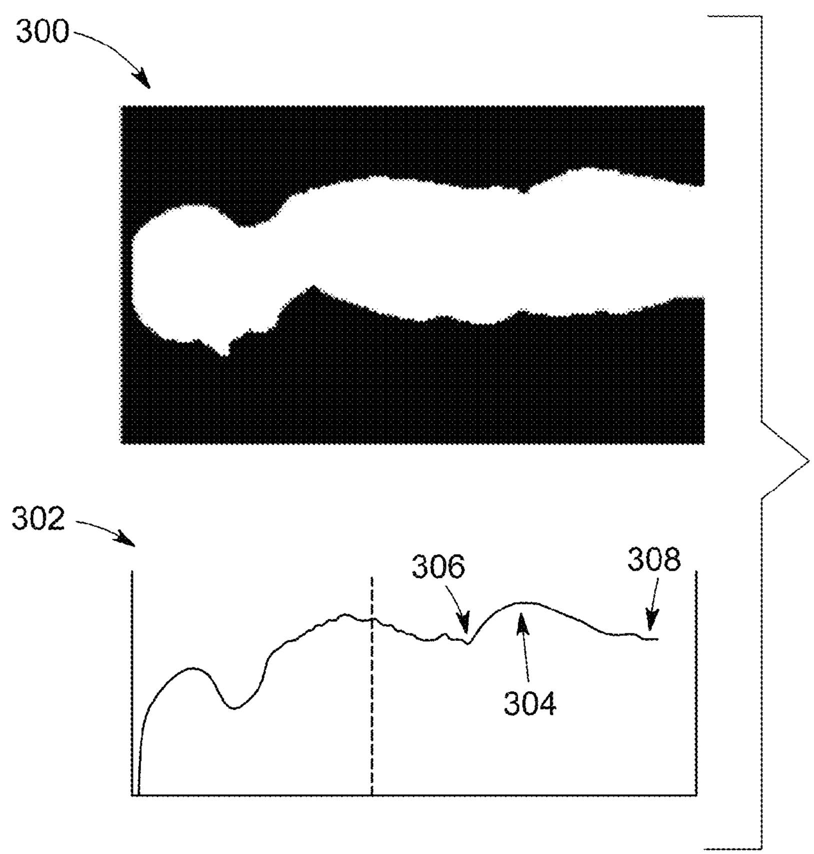
FIG. 11 is an embodiment of a body mask illustrated along a sagittal plane of the patient, and a plot denoting the contour of the body mask as a function of position along the sagittal line, in accordance with an aspect of the present disclosure.

Moving now to FIG. 11, a portion 300 of the body mask oriented along the sagittal line is illustrated. A plot 302 corresponding to the mask contour as a function of position along the sagittal line is also illustrated. As depicted, the pelvis may be located as a local maximum 304 bounded by local minima 306, 308 corresponding to the patient's waist and legs, respectively.

In FIG. 12, a portion 310 of the body mask oriented along the coronal plane of the patient 26 is illustrated, along with a plot 312 of the mask contour as a function of position along the coronal plane. As depicted, the crotch may be located as an inset 314 in the mask contour proximate to, or intersected by, the sagittal line. In addition, it should be noted that the lung and pelvis stations may be corrected using an allometric measurement based on the crotch.

Once the various anatomies are localized and the body masks generated using any one or a combination of the above methods, as noted above with respect to FIG. 4, fat and water volumes are segmented from the whole body MR images as discussed with respect to block 188. Again, in accordance with present embodiments, the fat volumes may be segmented using the $I_f$, $I_w$, and $I_i$ channels obtained in block 180 using a two-step process. The two-step process includes a first step of estimating the intra-body air statistics and a second step of generating fat $I_{ffr}$ and water $I_{wfr}$ fraction images.

FIG. 13 illustrates example images that may be obtained in accordance with block 188. In FIG. 13 a series of images are illustrated including CT fat images 320 where the fat component window has been set to [−250, −20], in-phase MR images 322, segmented fat-water masks 324 generated using equations (3) and (4), and fat fraction images 326. Head slices 328, shoulder slices 330, and lung slices 332 are provided for each set. The in-phase MR images 322 may be as-acquired images having grayscale data (i.e., contrast) relating to the relative levels of both water and fat in the particular slices. The segmented water-fat masks 324 may be obtained by combining the fat fraction data and the water fraction data and setting a particular value for each of the water and fat signals. Thus, the presence of fat is represented using an absolute color (light grey) and the presence of water is represented using another absolute color (white). Further, as illustrated in a lung slice 334 and a shoulder slice 336 of the segmented fat-water mask set 324, because lung segmentation is separately performed, the lungs are presented as a different, third color (dark grey). Accordingly, the lung slice 334 is a quaternary image (i.e., a 4-class image), in which the fat is represented as a first color, water is represented as a second color, the lungs are represented as a third color, and the background is represented as a fourth color (black). It should be noted that in certain embodiments, auto-stitching may be performed after the generation of the quaternary or 4-class images to generate a whole-body 4-class image.

Figure 14:
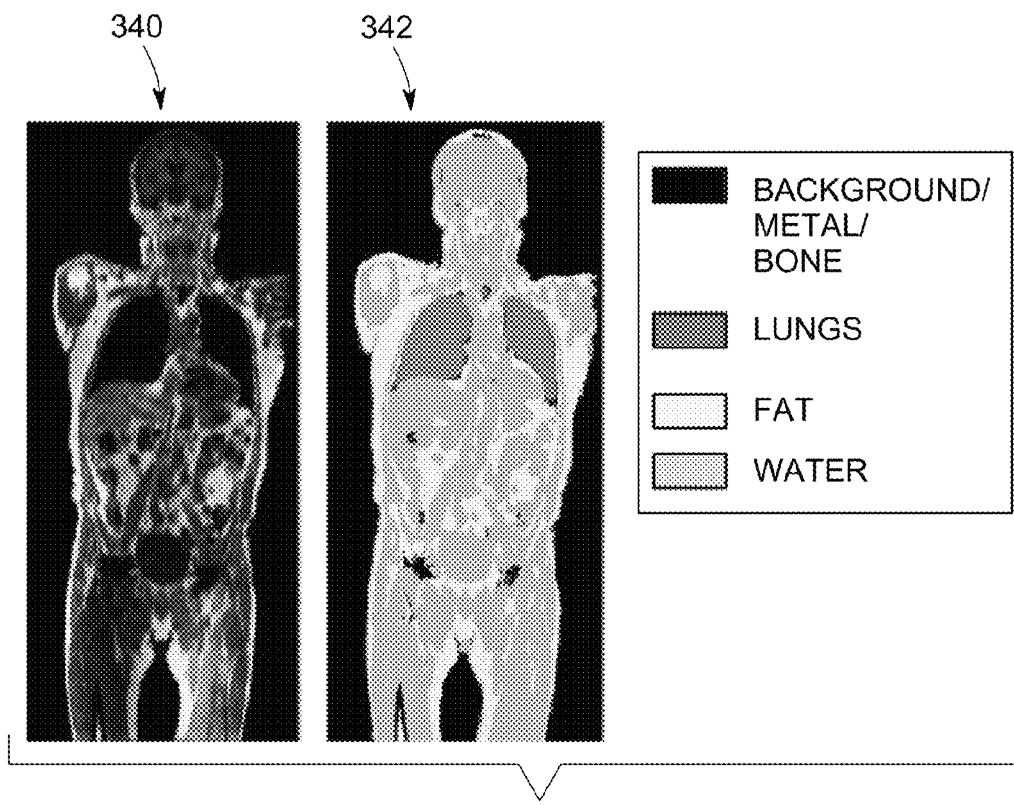
FIG. 14 is an embodiment of a multi-class segmented mask produced from a whole-body MRI scan, in accordance with an aspect of the present disclosure.

FIG. 14 illustrates an example in-phase MR image 340 and a four-class segmentation image 342 obtained in accordance with present embodiments. The 4-class segmentation image 342, as illustrated, includes background, metal, and bone as a single attenuating component, lungs as a second attenuating component, fat as a third attenuating component, and water as a fourth attenuating component. To enable attenuation correction in PET images, attenuation values obtained from a CT image may be assigned to the various classes of materials in the image 342. For example, the background/air may be assigned an attenuation value of 0 $mm^{-1}$, lungs may be assigned 0.0018 $mm^{-1}$, fat may be assigned 0.0086 $mm^{-1}$, and water may be assigned 0.01 $mm^{-1}$. Each tissue in the MR images may be treated as including fat, water, or a combination thereof. Accordingly, attenuation values may be assigned according to tissue labels obtained from the segmentation of fat and water images.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:

causing a magnetic resonance (MR) imaging system to perform a magnetic resonance (MR) imaging sequence to acquire MR image slices or volumes of a first station representative of a portion of a patient;

applying a first phase field algorithm to the first station to determine a body contour of the patient in the first station;

identifying a contour of a first anatomy of interest within the body contour of the first station using the first phase field algorithm or a second phase field algorithm;

segmenting the first anatomy of interest based on the identified contour of the first anatomy of interest;

correlating first attenuation information to the segmented first anatomy of interest;

acquiring a positron emission tomography image;

modifying the positron emission tomography (PET) image based at least on the first correlated attenuation information;

perform a magnetic resonance (MR) imaging sequence to acquire respective MR image slices or volumes of a plurality of additional stations;

modeling a containership of fat within bone marrow for every station in which the patient's bone is present to determine a cortical bone contour; and segmenting the cortical bone based on the cortical bone contour to generate a cortical bone mask.

2. The method of claim 1, comprising:

performing the MR imaging sequence in a station-wise manner to acquire respective MR image slices or volumes for a second station after acquiring the first station;

applying the first phase field algorithm to the second station to determine the body contour of the patient in the second station;

identifying a contour of a second anatomy of interest within the body contour of the second station using the first phase field algorithm or the second phase field algorithm;

segmenting the second anatomy of interest based on the identified contour of the second anatomy of interest;

correlating second attenuation information to the segmented second anatomy of interest; and modifying the PET image based at least on the second correlated attenuation information.

3. The method of claim 2, comprising identifying the first and second stations based on an analysis of the body contour, based on digital imaging and communications in medicine (DICOM) information, based on user-provided input, or based on information related to previously-acquired stations, or any combination thereof.

4. The method of claim 3, comprising stitching at least the first and second stations together to obtain a combined volumetric image of the patient and a 3D representation of the patient's body contour in the combined image.

5. The method of claim 4, wherein applying the first phase field algorithm to the first station to determine the body contour of the patient in the first station is commenced immediately after acquiring the respective MR image slices or volumes for the first station and before obtaining the combined volumetric image.

6. The method of claim 4, comprising modifying the PET image on a station-wise, prospective basis such that the PET image is iteratively modified after correlating respective attenuation information to each of the first and second stations.

7. The method of claim 4, wherein the combined volumetric image is obtained before applying the first phase field algorithm to the first station to determine the body contour of the patient in the first station.

8. The method of claim 1, wherein correlating the attenuation information to the segmented anatomy of interest comprises generating a pseudo-computed tomography (CT) image comprising the attenuation information correlated to the anatomy of interest.

9. The method of claim 8, wherein the PET image is corrected based on the pseudo-CT image.

10. The method of claim 1, wherein performing the MR imaging acquisition comprises performing at least one of Liver Acquisition with Volume Acquisition (LAVA)-Flex acquisition or Iterative Decomposition of water and fat with Echo Asymmetry and Least squares estimation (IDEAL) acquisition, and wherein the MR image slices or volumes of the first station include a fat image, a water image, an in-phase image, and an out-of-phase image for each slice selection of the acquisition, and the phase field algorithm uses a term combining complex MRI image data having both magnitude and phase from at least the fat image, the water image, and the in-phase image.

11. The method of claim 1, wherein the phase field algorithm models the boundary between the patient's subdermal fat or skin layer and the air surrounding the patient to determine the patient's body contour.

12. The method of claim 1, comprising:

performing the magnetic resonance (MR) imaging sequence to acquire respective MR image slices or volumes of the first station and a plurality of additional stations;

modeling a boundary between intra-body air and patient tissue to determine an intra-body air contour for every station;

modeling a boundary between intra-cranial air and patient tissue to determine a sinus contour;

modeling a boundary between tissue surrounding the patient's lungs and trachea and the air within the lungs and trachea to determine a lung and trachea contour;

segmenting the intra-body air contour, the sinus contour, and the patient's lungs and trachea contour to generate an intra-body air mask, a sinus mask, and a lung and trachea mask.

13. One or more tangible, non-transitory, machine-readable media storing instructions executable by a processor to perform the acts of:

causing a magnetic resonance (MR) imaging system to perform an MR imaging sequence to acquire MR image slices or volumes of a first station representative of a portion of a patient;

applying a first phase field algorithm to the first station to determine a body contour of the patient in the first station;

identifying a contour of a first anatomy of interest within the body contour of the first station using the first phase field algorithm or a second phase field algorithm;

segmenting the first anatomy of interest based on the identified contour of the first anatomy of interest;

correlating first attenuation information to the segmented first anatomy of interest;

acquiring a positron emission tomography image;

modifying the positron emission tomography (PET) image based at least on the first correlated attenuation information;

perform a magnetic resonance (MR) imaging sequence to acquire respective MR image slices or volumes of a plurality of additional stations;

modeling a containership of fat within bone marrow for every station in which the patient's bone is present to determine a cortical bone contour; and segmenting the cortical bone based on the cortical bone contour to generate a cortical bone mask.

14. The media of claim 13, comprising the phase field algorithm, wherein the phase field algorithm uses a term combining complex MR image data having magnitude and phase information from at least a fat image, a water image, and an in-phase image obtained for each slice selection of the MR acquisition.

15. The media of claim 13, comprising additional instructions that, when executed by the processor, are configured to model a boundary between intra-body air and patient tissues, to model containership of fat within bone marrow, and to model fat contours to generate a lung mask, a sinus mask, an intra-body air mask, a cortical bone mask and the body contour.

16. A hybrid positron emission tomography/magnetic resonance (PET/MR) imaging system, comprising:

an opening configured to receive a patient;

a primary field magnet;

a plurality of gradient field coils disposed about the opening;

a radiofrequency (RF) transmit coil;

a plurality of RF receiving coils;

a photodetector disposed about the opening and configured to detect positron emissions from the patient to generate signals representative of the detected positrons; and control circuitry coupled to the gradient field coils, to the RF transmit coil, to the plurality of RF receiving coils, and to the photodetector, wherein the control circuitry is configured to:

apply control signals to the gradient, RF transmit and receiving coils to perform an MR imaging sequence to acquire MR image slices or volumes of a first station representative of a portion of the patient;

process data generated by the photodetector as a result of detecting positrons to generate a PET image of the patient; and perform a PET image reconstruction process comprising:

applying a first phase field algorithm to the first station to determine a body contour of the patient in the first station;

identifying a contour of a first anatomy of interest within the body contour of the first station using the first phase field algorithm or a second phase field algorithm;

segmenting the first anatomy of interest based on the identified contour of the first anatomy of interest;

modifying the PET image based at least on a continuous distribution map or a pseudo-CT image derived from data related to the MR image slices;

perform a magnetic resonance (MR) imaging sequence to acquire respective MR image slices or volumes of a plurality of additional stations;

modeling a containership of fat within bone marrow for every station in which the patient's bone is present to determine a cortical bone contour; and segmenting the cortical bone based on the cortical bone contour to generate a cortical bone mask.

17. The system of claim 16, wherein the control circuitry is configured to apply control signals to the gradient, RF transmit and receiving coils to perform the MR imaging sequence in a station-wise manner to acquire respective MR image slices or volumes for a plurality of additional stations after acquiring the first station, and the PET image reconstruction process comprises:

applying the first phase field algorithm to the additional stations to determine the body contour of the patient in the additional stations;

identifying a contour of at least a second anatomy of interest within the body contour of the additional stations using the first phase field algorithm or the second phase field algorithm; and segmenting the second anatomy of interest based on the identified contour of the second anatomy of interest.

18. The system of claim 17, wherein the PET image reconstruction process comprises identifying at least one of the plurality of additional stations based on an analysis of the body contour, based on allometric ratios of body contour mask or Dixon images, or based on digital imaging and communications in medicine (DICOM) information, based on user-provided input, or based on information related to previously-acquired stations, or any combination thereof.

* * * * *